United States Patent [19]

Heikonen et al.

[11] Patent Number: 4,751,089

[45] Date of Patent: Jun. 14, 1988

[54] COMPOSITION AND METHOD FOR ENSILAGING FODDER AND GRAIN

[75] Inventors: Matti Heikonen, Espoo; Tauno Moisio, Helsinki; Matti Harju, Nummela, all of Finland

[73] Assignee: Suomen Sokeri Oy, Kantvik, Finland

[21] Appl. No.: 861,120

[22] Filed: May 7, 1986

Related U.S. Application Data

[63] Continuation of Ser. No. 624,680, filed as PCT FI83/00067, Nov. 1, 1983, published as WO84/01694, May 10, 1984.

[30] Foreign Application Priority Data

Nov. 2, 1982 [FI] Finland .................................. 823736

[51] Int. Cl.$^4$ ........................... A23K 1/00; A23K 3/00
[52] U.S. Cl. ......................................... 426/53; 426/52; 426/54; 426/335; 426/532; 426/807
[58] Field of Search ................. 426/2, 52, 53, 54, 331, 426/807, 335, 532

[56] References Cited

U.S. PATENT DOCUMENTS

| 1,629,077 | 5/1927 | Holken | 426/54 |
|---|---|---|---|
| 2,799,583 | 7/1957 | Harris | 426/69 |
| 3,184,314 | 5/1965 | Forest et al. | 426/331 |

FOREIGN PATENT DOCUMENTS

| 213741 | 3/1956 | Australia | 426/54 |
|---|---|---|---|
| 2125038 | 12/1971 | Fed. Rep. of Germany . | |
| 3005020 | 8/1980 | Fed. Rep. of Germany . | |
| 2046567 | 11/1980 | United Kingdom | 426/54 |

OTHER PUBLICATIONS

Kogyo Derwent Abstract, "Stabilizer Preventing Undesirable Changes in Foods" (1970).
Wesley "Glucose Oxidase Treatment Prolong Shelf Life of Fresh Seafood" Food Development, Jan. 1982, pp. 36–38.
Food Science and Technology Abstract, vol. 9, No. 7 (1977), abstract No. 7J 1002 (Przemysl Fermentacyjny i Rolny 20 (10), pp. 18–19 (1976).
Wesley, "Glucose Oxidase Treatment Prolongs Shelf Life of Fresh Seafood", Food Development, vol. 16 (1), pp. 36–38 (1982).

*Primary Examiner*—R. B. Penland
*Attorney, Agent, or Firm*—Brumbaugh, Graves, Donohue & Raymond

[57] ABSTRACT

The invention relates to a composition and method for ensiling fodder and grain. The composition contains glucose oxidase in a carrier medium in an amount effective to produce gluconic acid upon addition to the material to be ensiled. A suitable amount of glucose oxidase to be added is from 10,000 to 10,000,000 IU per ton of material to be ensiled.

32 Claims, No Drawings

COMPOSITION AND METHOD FOR ENSILAGING FODDER AND GRAIN

This application is a continuation of application Ser. No. 624,680, filed as PCT FI83/00067 on Nov. 1, 1983, published as WO84/01694 on May 10, 1984, abandoned.

The present invention relates to a composition and a method for ensilaging fodder and grain.

In ensilage preparation the grass is chopped to facilitate packing. Natural anaerobic fermentation of soluble carbohydrates (sugars) then results in the production of acids mainly lactic acid, which prevents further microbial breakdown and thus the fodder can be preserved for long periods of time. The grass is packed and covered to achieve airtight storage. Natural oxidation (breathing) and fermentation removes the oxygen from the mass whereafter the anaerobic lactic fermentation takes over. The pH of grass is about 6.

A. I. Virtanen's well known studies show that the pH of a silage must be about 4, preferably below it, in order to prevent unwanted biological reactions. Previously the pH has been lowered primarily by natural fermentation. Anaerobic lactic fermentation is necessary to achieve the low pH range. One method to lower the pH is by the addition of mineral acids, acid salts or organic acids. Addition of soluble sugars improves the lactic fermentation of crops deficient in free sugars. The amount of free sugars can also be increased by addition of enzymes such as cellulase, hemicellulase or $\beta$-glucosidase, which break down cellulose and polysaccharides. A further method to improve the lactic acid fermentation is to add lactic acid bacteria to the ensilage.

Preservatives such as formaldehyde, nitrites or sulphites have also been used to present unwanted reactions in the ensilage.

The prior art methods are not all together satisfactory. Nitrites and formaldehyde are harmful to the animals and do not remove oxygen. Optimal lactic acid fermentation cannot occur before anaerobic conditions are achieved. In natural fermentation the free fermentable sugars are consumed by the aerobic fermentations and oxidations thus leaving the fodder deficient in free sugars for the lactic fermentation. Frequently the lactic fermentation is not rapid or effective enough to prevent unwanted side fermentations.

It is an object of the present invention to provide a composition for ensiling fodder and grain by which the above drawbacks of the prior known ensiling preparations can be eliminated.

The invention is based on the known phenomenon that in the presence of glucose the glucose oxidase enzyme (GOD) system catalyses the following reactions:

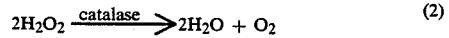

The produced oxygen is finally used up by the reaction (1) and the end product is gluconic acid. We have found that in the preparation of ensilage the enzymic reactions result in a rapid lowering of pH as well as removal of oxygen, both being essential for the lactic acid fermentation. The glucose oxidase enzyme or the end products of the reaction do not in any way prevent the lactic acid fermentation. Maximal gluconic acid concentrations are achieved in 2 to 20 hours whereafter the lactic acid concentration is increasing while the gluconic acid concentration is simultaneously decreasing.

The present invention thus provides a composition for ensiling fodder and grain, containing glucose oxidase in a carrier medium in an amount effective to produce gluconic acid upon addition to said material to be ensiled.

The composition of the invention is advantageously in the form of an aqueous solution containing glucose oxidase having an activity of about 100,000–1,000,000 international units (IU) per liter. The composition can, however, also be in dried form which is diluted with water prior to use.

The glucose oxidase IU unit (international unit) is defined as the amount of enzyme required to use 10 microliters of oxygen per minute with a substrate containing 3.3% of glucose in phosphate buffer pH 5.9 at 35° C. in the presence of excess oxygen.

The composition of the invention may also contain in addition to glucose oxidase one or several of the enzymes catalase, invertase, cellulase, hemicellulase, and $\beta$-glucosidase. The object of the enzyme ingredients is to promote the formation of glucose to be further converted to gluconic acid by the action of glucose oxidase. Cellulase preparations usually contain also hemicellulase which may also be added separately. Several cellulases contain also $\beta$-glucosidase. The enzymes may be purified enzyme preparations or dried cell masses.

It is also advantageous to include sugar products in the composition of the invention. Such sugar products are, for example, beet or cane molasses or whey hydrolyzates, starch hydrolyzates or wood hydrolyzates, which contain free hexoses and/or pentoses.

Other optional ingredients of the composition are either inorganic acids, such as sulfuric, hydrochloric or phosphoric acid, or organic acids, such as formic, acetic, lactic, or gluconic acid. The purpose of the acids is to lower the initial pH of the material to be ensiled to pH 4 to 6, which is optimal. Further the composition may include salts, such as magnesium, calcium, or urea phosphate or calcium or sodium formate, and preservatives, such as sorbate, benzoate or sodium nitrite.

The composition is preferably prepared to contain standardized amounts of enzymes and other ingredients making up the bulk of said beet or cane molasses or whey hydrolyzate or starch hydrolyzate or wood hydrolyzate. The composition can be prepared to suit fodder, grain or any other material to be ensiled. The composition may be in the form of a solution or dried, pulverized or granulated. The enzymes may be purified enzyme preparations or dried cell masses.

Suitable amounts of the above ingredients, when present in the composition, to be added to one ton of materials to be ensiled are as follows:

| | |
|---|---|
| Glucose oxidase | 10,000 to 10,000,000 IU |
| Catalase | 500 to 5,000,000 Baker units |
| Cellulase | 1,000,000 to 100,000,000 HEC units |
| $\beta$-glucosidase | 100,000 to 10,000,000 nkat units |
| Molasses, wood hydrolyzate, whey hydrolyzate or starch hydrolyzate | 0.5 to 20 kg calculated as dry matter |
| Mineral or organic acids | 1 to 2 l |
| Salts | 1 to 5 kg |

-continued

| Preservatives | 0.2 to 1 kg |
|---|---|

As to the activity units of the various enzymes, reference is made to the following literature:
Catalase Baker's units: Scott D. and Hammer F. Enzymologia 22 (1960) 194–200.
Cellulase HEC units: Loewenberg J. and Chapman C.: Arch. Microbiol. 113 (1977) 61–64.
$\beta$-glucosidase: Bailey M. and Nevalainen K.: Enzyme Microb. Technol. 3 (1981) 153–157.

The invention also relates to a method for ensiling fodder and grain, such method comprising adding to the material to be ensiled glucose oxidase in a carrier medium in an amount effective to produce gluconic acid to lower the pH of the material and consume oxygen. As already mentioned above, such effective amount may comprise from 10,000 to 10,000,000 IU of glucose oxidase per ton of material to be ensiled. The method of the invention also includes addition of the above-mentioned other ingredients in various combinations and in the amounts indicated.

The composition and method of the invention are further illustrated by the following examples.

EXAMPLE 1

To fresh chopped grass was added 0.005% by weight of glucose oxidase preparation (Finnish Sugar Co. Ltd.) having an activity of 11,250 IU/ml and catalase activity 2500 Baker units/ml. Table 1 shows the formation of gluconic acid and lowering of pH during 24 hours.

TABLE 1

Formation of gluconic acid and lowering of pH of grass silage in 24 hours.

| Sample | Gluconic acid % | pH |
|---|---|---|
| reference | 0.01 | 6.3 |
| 0.005% GOD | 1.20 | 5.1 |

EXAMPLE 2

To fresh grass was added acids, cellulase and glucose oxidase as shown in table 2.

TABLE 2

Composition of silages % of silage

| Additives | Samples | | | | |
|---|---|---|---|---|---|
| | 1 | 2 | 3 | 4 | 5 |
| AIV II-solution % | 0 | 0.5 | 0 | 0 | 0 |
| Cellulase % | 0 | 0.014 | 0.014 | 0.05 | 0 |
| Glucose oxidase % | 0 | 0.003 | 0.003 | 0.01 | 0.01 |

The AIV II-solution consisted of 80% formic and 20% phosphoric acid. The cellulose activity of the enzyme preparation was 32,000 HEC units/ml and the $\beta$-glucosidase activity was 1,500 nkat/ml. This enzyme preparation was made by Alko Ltd. The glucose oxidase was same as in example 1.

Tables 3, 4, and 5 present analysis of the silage liquids. Table 3 represents a sample after 24 hours, table 4 after a month and table 5 after two months.

TABLE 3

Analysis of silage liquids after 24 hours.

| | 1 | 2 | 3 | 4 | 5 |
|---|---|---|---|---|---|
| pH | 6.6 | 4.0 | 5.6 | 5.2 | 5.2 |
| Sugars g/l | 15 | 20 | 15 | 20 | 15 |
| Acidity as lactic acid g/l | 3.1 | 14.0 | 6.3 | 8.2 | 8.8 |
| Ammonia g/l | 0.1 | 0.1 | 0.2 | 0.2 | 0.1 |

TABLE 4

Analysis of silage liquids after a month.

| | 1 | 2 | 3 | 4 | 5 |
|---|---|---|---|---|---|
| pH | 6.6 | 4.5 | 4.5 | 4.3 | 5.0 |
| Sugars g/l | 0 | 12.5 | 0 | 2.5 | 2.5 |
| Lactic acid g/l | 0.8 | 1.4 | 12.5 | 30.6 | 13.2 |
| Gluconic acid g/l | 0 | 3.8 | 0 | 0 | 0.03 |
| Butyric acid g/l | 0 | 0 | 0 | 0 | 0 |
| Acidity as lactic acid g/l | 5.4 | 11.3 | 23.0 | 27.9 | 10.4 |
| Ammonia g/l | 0.8 | 0.4 | 0.6 | 0.8 | 0.8 |

TABLE 5

Analysis after 2 months.

| | 1 | 2 | 3 | 4 | 5 |
|---|---|---|---|---|---|
| pH | 5.3 | 4.2 | 4.6 | 4.1 | 5.0 |
| Sugars g/l | 0 | 2.5 | 0 | 0 | 0 |
| Lactic acid g/l | 1.4 | 7.4 | 7.9 | 14.2 | 16.5 |
| Gluconic acid g/l | 0 | 1.1 | 0 | 0 | 0 |
| Butyric acid g/l | 0.8 | 0.1 | 0 | 0 | 0 |
| Acidity as lactic acid g/l | 13.7 | 21.2 | 27.0 | 30.6 | 13.1 |
| Ammonia g/l | 2.0 | 0.4 | 0.6 | 0.4 | 0.8 |

Table 3 shows how the glucose oxidase addition rapidly lowers the pH and removes the oxygen. Tables 4 and 5 show the effect of cellulase. It is clear that the enzyme has increased the amount of fermentable sugars, which results in a lower pH and higher acidity compared to the reference. Table 5 also shows that the enzyme addition has prevented the unwanted butyric acid fermentation and the formation of ammonia from proteins.

EXAMPLE 3

To fresh chopped grass was added acid salts (Mg-, Ca- and urea phosphate and Ca- and Na-formate and NaCl), cellulase and glucose oxidase as shown in table 6.

TABLE 6

| | Composition % by weight | |
|---|---|---|
| | silage 1 | silage 2 |
| Acid salt mixture % | 0.4 | 0.4 |
| Cellulase % | 0 | 0.05 |
| Glucose oxidase % | 0 | 0.005 |

The cellulase and glucose oxidase preparations were same as in example 1. Table 7 shows silage analysis after 24 hours.

TABLE 7

Silage analysis after 24 hours. (The results represent means from several samples).

| | Silage 1 | Silage 2 |
|---|---|---|
| Dry substance % | 22 | 22 |
| Sugars % | 4.5 | 5.0 |
| pH | 6.0 | 5.1 |
| Acetic + lactic acid % | 0 | 0 |
| Gluconic acid % | 0 | 1.0 |

Table 7 shows that the glucose oxidase was active also in the presence of acid salts.

EXAMPLE 4

To fresh chopped barley was added 0.005% by weight of glucose oxidase preparation, which was the same as in example 1. Table 8 shows the formation of gluconic acid during the first 24 hours.

TABLE 8

Formation of gluconic acid in barley ensilage during 24 hours. Glucose oxidase added 0.005% by weight.

| Time from preparation of ensilage | Gluconic acid in ensilage liquid |
| --- | --- |
| 2 h | 0.71% |
| 15 h | 1.31% |

Table 8 shows that the glucose oxidase was active in barley ensilage lowering the pH and removing oxygen.

EXAMPLE 5

Fodder ensilage composition.

To an enzymatically hydrolyzed whey solution, which contained 70% by weight of dry matter consisting of mainly glucose and galactose were added:
15 ml/l of glucose oxidase-catalase enzyme preparation having a glucose oxidase activity of 11,250 IU/ml, and catalase activity 2,500 Baker units/ml, and 500 ml/l of cellulase-glucosidase enzyme preparation having a cellulase activity 32,000 HEC/ml.

For final use 1 liter of the composition was diluted with water to 5 liters. The diluted mixture was mixed with 1 ton of ensilage.

EXAMPLE 6

To a wood hydrolyzate solution containing 35% by weight of dry matter consisting mainly of pentose sugars were added:
10 ml/l glucose oxidase preparation
400 ml/l cellulase preparation
200 g/l sodium benzoate The same enzyme preparations were used as in example 1. For use the solution was diluted with water by adding 2 liters of water per 1 liter of solution. 5 liters of the diluted solution were used for 1 ton of ensilage.

EXAMPLE 7

Two solutions were prepared:
(1) Sugar solution.

Whey was treated with beta-galactosidase until about 90% of the lactose was hydrolyzed to glucose and galactose. The solution was evaporated to 60% by weight of dry matter and glucose added to a concentration of 70% by weight of dry matter. 0,5% Tween 20 ® (surface active agent) was added to the concentrated solution.

(2) Glucose oxidase preparation (Finnish Sugar Co. Ltd.).

A glucose oxidase preparation having an activity of 11,250 IU/ml was prepared by fermentation of an Aspergillus niger strain. (The method is conventional.)

Before use 7 liters of the sugar solution (1) was diluted with 15 liters of water in a 30 liter tank. To the diluted solution was added 70 ml of glucose oxidase preparation (2) and mixed well. 5 liters of this solution were added to 1 ton of grass in the mowing machine. The fodder mixture was transferred to the storage, covered and packed. Samples were taken from the storage after 24 hours. The samples contained 0.7-1.3% of gluconic acid, the pH was 5.1-5.3. At this stage the lactic fermentation took over and rapidly reduced the pH to about 4.

From a parallel storage the gas formation was measured by means of a "Drägerwerke AG" tube. The measurement showed that oxygen was removed and conditions for the lactic fermentation achieved within a few hours.

EXAMPLE 8

Beet sugar molasses (the main sugar being sucrose) was diluted with water to 70% by weight of dry matter and the following ingredients added:
20 ml/l glucose oxidase preparation
200 ml/l cellulase preparation
200 g/l sodium benzoate The same enzyme preparations were used as in examples 6 and 7.

Before use 1 liter of the mixture was diluted with water to 5 liters. 5 liters of the diluted solution were mixed with 1 ton of fodder ensilage.

We claim:

1. A composition for ensilaging a material selected from the group consisting of fodder and grain, comprising glucose oxidase and catalase and one or more enzymes selected from the group consisting of cellulases, hemicellulases, and glucosidases in a carrier medium in an amount effective to produce gluconic acid upon addition to the material to be ensiled.

2. A composition as in claim 1 in the form of an aqueous solution wherein the glucose oxidase has an activity of 10,000 to 12,500 IU/ml.

3. A composition as in claim 2 and further containing a material selected from the group consisting of wood hydrolyzate, whey hydrolyzate, starch hydrolyzate, beet molasses, cane molasses, and combinations thereof.

4. A composition as in claim 3 and further containing an acid selected from hydrochloric, sulfuric, phosphoric, formic, acetic, lactic and gluconic acid.

5. A composition as in claim 3 and further containing lactic acid bacteria.

6. A composition as in claim 3 and further containing a surfactant.

7. A composition as in claim 3 and further containing a preservative.

8. A composition comprising a material to be ensiled selected from the group consisting of fodder and grain and exogenous glucose oxidase in a carrier medium, said glucose oxidase being present in an amount effective to produce gluconic acid and lower the pH to between 4 and 6 whereby lactic acid fermentation is enhanced.

9. A composition according to claim 8, wherein the glucose oxidase has an activity of 10,000 to 10,000,000 IU per ton of material to be ensiled.

10. A composition according to claim 9, additionally comprising exogenous catalase.

11. A composition according to claim 10, additionally comprising one or more exogenous enzymes selected from the group consisting of cellulases, hemicellulases and glucosidases.

12. A composition according to claim 9 additionally comprising one or more materials selected from the group consisting of wood hydrolyzate, whey hydrolyzate, starch hydrolyzate, beet molasses, and cane molasses.

13. A composition as in claim 12 and further containing an exogenous acid selected from the group consisting of hydrochloric, sulfuric, phosphoric, formic, acetic, lactic and gluconic acid.

14. A composition according to claim 13, additionally comprising one or more exogenous enzymes selected from the group consisting of cellulases, hemicellulases and glucosidases.

15. A composition according to claim 12, additionally comprising exogenous catalase.

16. A composition according to claim 9, additionally comprising exogenous catalase.

17. A composition according to claim 16, additionally comprising one or more exogenous enzymes selected from the group consisting of cellulases, hemicellulases and glucosidases.

18. A composition according to claim 16 additionally comprising one or more materials selected from the group consisting of wood hydrolyzate, whey hydrolyzate, starch hydrolyzate, beet molasses, and cane molasses.

19. A composition as in claim 12 or 16 and further containing exogenous lactic acid bacteria.

20. A composition as in claim 12 or 16 and further containing a surfactant.

21. A composition as in claim 12 or 16 and further containing a preservative.

22. A method for ensilaging a material selected from the group consisting of fodder and grain, comprising adding to the material to be ensiled glucose oxidase in a carrier medium in an amount effective to produce gluconic acid, to lower the pH of the material and consume oxygen.

23. A method as in claim 22, comprising adding glucose oxidase in an amount of from 10,000 to 10,000,000 IU per ton of material to be ensiled.

24. A method as in claim 23, comprising further adding at least one enzyme selected from the group consisting of cellulase, hemicellulase, and β-glucosidase and combinations thereof.

25. A method as in claim 24, comprising adding cellulase in an amount of from 1,000,000 to 100,000,000 HEC units per ton of material to be ensiled.

26. A method as in claim 24, comprising adding β-glucosidase in an amount of from 100,000 to 10,000,000 nkat units per ton of material to be ensiled.

27. A method as in claim 23, comprising further adding catalase to the material to be ensiled.

28. A method as in claim 27, comprising adding catalase in an amount of 500 to 5,000,000 Baker units per ton of material to be ensiled.

29. A method as in claim 27, comprising further adding a material selected from the group consisting of wood hydrolyzate, whey hydrolyzate, starch hydrolyzate, beet molasses, cane molasses and combinations thereof.

30. A method as in claim 29, comprising adding said material in an amount of 0.5 to 20 kg calculated as dry matter per ton of material to be ensiled.

31. A method as in claim 23, comprising further adding an acid selected from hydrochloric, sulfuric, phosphoric, formic, acetic, lactic and gluconic acid.

32. A method as in claim 31, comprising adding said acid in an amount of from 1 to 2 liters per ton of material to be ensiled.

* * * * *